(12) United States Patent
De Freitas Silva et al.

(10) Patent No.: US 11,311,055 B2
(45) Date of Patent: Apr. 26, 2022

(54) SOCK FOR PREVENTING ANKLE INJURY

(71) Applicant: PEÚGAS CARLOS MAIA, LDA, Vila Nova de Famalicão (PT)

(72) Inventors: Diogo César De Freitas Silva, Vila Nova de Gaia (PT); Alfredo Alexandre Tomé Lopes, Senhora da Hora Matosinhos (PT); Flávio Miguel Ferreira Da Silva Maia, Vila Nova de Famalicão (PT); Emanuel José De Campos Simões, Vila Nova de Famalicão (PT)

(73) Assignee: PEÚGAS CARLOS MAIA, LDA, Carreira (PT)

( * ) Notice: Subject to any disclaimer, the term of this patent is extended or adjusted under 35 U.S.C. 154(b) by 0 days.

(21) Appl. No.: 16/622,821

(22) PCT Filed: Jun. 27, 2018

(86) PCT No.: PCT/IB2018/054764
§ 371 (c)(1),
(2) Date: Dec. 13, 2019

(87) PCT Pub. No.: WO2019/003145
PCT Pub. Date: Jan. 3, 2019

(65) Prior Publication Data
US 2021/0145079 A1    May 20, 2021

(30) Foreign Application Priority Data
Jun. 27, 2017 (PT) .......................................... 110168

(51) Int. Cl.
*A61F 5/01* (2006.01)
*A61F 13/06* (2006.01)
*A41B 11/00* (2006.01)

(52) U.S. Cl.
CPC ........... *A41B 11/003* (2013.01); *A61F 5/0111* (2013.01); *A61F 13/066* (2013.01); *A41B 2400/32* (2013.01)

(58) Field of Classification Search
CPC . A41B 11/003; A41B 2400/32; A61F 13/066; A61F 5/0111
See application file for complete search history.

(56) References Cited

U.S. PATENT DOCUMENTS 5,640,714 A * 6/1997 Tanaka .................. A41B 11/00
2/22
5,898,948 A   5/1999 Kelly
(Continued)

FOREIGN PATENT DOCUMENTS

DE    202011105360    11/2011

*Primary Examiner* — Katharine G Kane
(74) *Attorney, Agent, or Firm* — Leason Ellis LLP

(57) ABSTRACT

The present disclosure relates to a sock for preventing ankle injury of a subject, comprising a sock body which includes a leg section and a foot section, wherein the leg section comprises a fixation band comprising a first zone of high compression, configured to contour the transversal leg subject body, wherein the foot section comprises a second zone of high compression positioned to match the back of the ankle of the subject and configured to minimize subject adduction/abduct ion movements; a third zone of high compression that bounds to the subject leg section and foot section with a X-shape that begins in the fixation band and contours the plant of the foot section and the upper part of the foot section, configured to restrict the movement of subject plantar flexion, namely eversion/inversion movements, wherein the first zone and the second zone of high compression are bound by a vertical band, wherein such vertical band accompanies laterally the peroneal alignment path of the subject ending in the fixation band, wherein the remaining zones are low compression zones.

12 Claims, 6 Drawing Sheets

(56) References Cited

U.S. PATENT DOCUMENTS

| | | | |
|---|---|---|---|
| 7,441,419 B1* | 10/2008 | Dollyhite | A61F 13/08 66/178 A |
| 10,398,584 B2* | 9/2019 | Iida | A61F 5/0111 |
| 2003/0230121 A1* | 12/2003 | Yokoyama | A41B 11/003 66/178 A |
| 2006/0247566 A1* | 11/2006 | Gobet | A61F 13/08 602/62 |
| 2007/0149908 A1 | 6/2007 | Gordon, Jr. | |
| 2007/0283483 A1* | 12/2007 | Jacober | D04B 1/265 2/239 |
| 2008/0306422 A1 | 12/2008 | McChesney | |
| 2009/0005717 A1* | 1/2009 | Brzank | A61F 5/0111 602/65 |
| 2009/0013450 A1* | 1/2009 | Lambertz | A61F 13/066 2/239 |
| 2009/0105623 A1* | 4/2009 | Albrecht | A61H 9/0092 602/27 |
| 2009/0126081 A1* | 5/2009 | Lambertz | A41B 11/003 2/239 |
| 2009/0165190 A1* | 7/2009 | Araki | D04B 1/02 2/240 |
| 2011/0015668 A1* | 1/2011 | Cros | D04B 1/265 606/201 |
| 2011/0314591 A1* | 12/2011 | Mitsuno | A61F 13/08 2/239 |
| 2012/0035510 A1* | 2/2012 | Cros | D04B 1/265 600/592 |
| 2012/0071806 A1* | 3/2012 | Matthews | A61F 5/0111 602/27 |
| 2012/0078152 A1* | 3/2012 | Robertson | A61F 5/0111 602/27 |
| 2012/0102625 A1* | 5/2012 | Klein | D04B 1/04 2/239 |
| 2012/0184887 A1* | 7/2012 | Wynne | A61F 5/03 602/19 |
| 2012/0238929 A1* | 9/2012 | Grunden | A61F 5/0111 602/27 |
| 2013/0131572 A1* | 5/2013 | Cros | A61F 5/40 602/75 |
| 2014/0053610 A1* | 2/2014 | Fukui | A41B 11/003 66/183 |
| 2014/0058311 A1* | 2/2014 | Higgins | A61F 13/064 602/63 |
| 2014/0276321 A1* | 9/2014 | Sellitto | A61F 5/0127 602/29 |
| 2014/0331387 A1* | 11/2014 | Hennings | A41B 11/003 2/239 |
| 2015/0119781 A1 | 4/2015 | Ponce | |
| 2015/0173428 A1* | 6/2015 | Langer | A41D 13/0015 2/227 |
| 2016/0166419 A1* | 6/2016 | Jones | D04B 1/26 602/66 |
| 2016/0206462 A1* | 7/2016 | Iida | A61F 13/066 |
| 2018/0021199 A1* | 1/2018 | Halbrecht | A61H 1/008 601/27 |
| 2018/0051401 A1* | 2/2018 | Giorgini | D04B 1/265 |

* cited by examiner

SOCK FOR PREVENTING ANKLE INJURY

CROSS-REFERENCE TO RELATED APPLICATIONS

This application is a U.S. National Stage Application under 35 U.S.C. § 371 of International Patent Application No. PCT/IB2018/054764, filed Jun. 27, 2018 which claims priority to Portugal Patent Application No. 110168, filed Jun. 27, 2017, the contents of which are each hereby incorporated by reference in their respective entireties.

TECHNICAL FIELD

The present disclosure relates to a sock for preventing ankle injury; a sock for providing additional protection for an ankle joint, reducing the need for using an ankle support. The sock of the present disclosure can be used in sports for preventing and reducing the ankle sprain.

BACKGROUND

The importance of intervening in the prevention of ankle sprain is supported by studies that place this type of injury as the most frequent in several individual and collective sports, which represent 80 to 100% of all injuries in this anatomical region in some sports[1,2].

Up to 650,000 ankle injuries can occur in a single country in Europe (Netherlands), with incidence rates of 1.5-7 per 1000 person-year in the European population in general[3].

It is also an injury with a high recurrence rate, and in about 40% of cases it may lead to Chronic Ankle Instability[2-4].

Its prevalence is of concern in Europe, but also in the rest of the world, regardless of age, sex and competitive level[2,5].

The socioeconomic impact on health systems is enormous, because each injury can reach values in the range of 360.60 € to 10,949.00 €, which multiplied by the total number of injuries can exceed 234 million euros per year[3,6].

Ankle sprain as a health problem has prevention as the best possible solution. Since preventive policies best serve the interests of general society, it is essential to focus on methods of simple application, transversal to the entire world population, that promote individual autonomy, foster an active lifestyle and improve the quality of life.

Thus, the ease of implementation of this preventive method in sports communities and in the general population, regardless of age, physical activity level or gender, makes this prevention method the perfect vehicle to benefit the largest number of people in the world.

Because it is such a frequent injury, any effective method of reducing the risk of injury will ultimately benefit thousands of people.

The fact that the socks are a piece of clothing essential to sports practice promotes adherence to the preventive program, since the user will hardly forget it. The same does not happen with the other available methods (ankle bandages and ankle supports) which, as an "additional" part of the sportswear, is often not added to the sports bag by forgetfulness.

These new socks will allow the user to maintain the same levels of sensitivity and/or perception to contact with the ball, a factor of extreme importance in sports such as soccer and futsal. On the other hand, the existing solutions, "ankle bandages+conventional socks" or "Ankle supports+conventional socks", reduce this sensitivity and/or perception, impairing the performance, namely of the assertiveness of the pass. When the athlete associates a preventive method to performance reduction, often lead to the poor adhesion to that preventive method. With these new socks solution, this problem does not arise.

In the economic point of view, expressed in the costs of acquiring sports equipment by the athlete or club, this new solution is intended to be advantageous since it is reusable (in contrast to functional bandages) and is part of the wearer's clothing, not appearing as an additional piece to the sportswear. Thus, the athlete/club would need to purchase only a sock, rather than buying conventional socks and additionally ankle supports.

Aware of the urgent premise of avoiding waste and encouraging reuse, these socks are a more environmentally friendly solution as they are a reusable prevention method. On the other hand, solutions such as functional bandages that do not allow their reuse and that use glues in their bands are completely disposable and non-transferable, which does not allow them to be a sustainable environmental solution.

These new socks will help solve the health and socioeconomic problems associated with this injury.

It is innovative concept will be incorporating in a single piece of clothing (socks), the theoretical foundations and characteristics of two methods widely used in the prevention of this injury (Ankle Supports and Functional bandages).

These facts are disclosed in order to illustrate the technical problem addressed by the present disclosure.

General Description

The present disclosure relates to a sock capable of providing additional protection for an ankle joint reducing the need for using an ankle support without reducing the performance/comfort of the subject.

The socks for preventing the ankle injury namely sprain. The socks of the present disclosure allow the primary, secondary and tertiary prevention of ankle sprain, while at the same time they enhance sports performance[7-9].

In an embodiment, the sock of the present disclosure may have four versions:
high socks to the knee (FIG. 1, 2, 3, 4, 5),
short socks to the middle of the leg (FIG. 7) and,
similar to the previous socks mentioned above but without the region of the fingers (FIG. 8).

In an embodiment, the sock of the present disclosure may comprise a mixture of elastane (4-7%) and polyamide (93-96%) fibres with different orientations.

In an embodiment, the sock of the present disclosure may have areas of external plantar adhesion (FIG. 5). However, in same embodiments the socks of the present disclosure may be produced without this component.

The present disclosure relates to a sock for preventing ankle injury of a subject, namely sprain, comprising a sock body which includes a leg section and a foot section
wherein the leg section comprises a fixation band comprising a first zone of high compression, (band 2a FIG. 1), preferably with a single or double U-shape, configured to contour the lower region of the sural triceps muscle, wherein the foot section comprises a second zone of high compression positioned; namely U-shaped band (Band 3, FIG. 4), to match the back of the ankle of the subject and configured to minimize subject adduction/abduction movements;
a third zone of high compression, preferably comprising two bands (2b and 2c, FIG. 2) that bounds to the subject leg section and foot section with a X-shape that begins in the fixation band (2a) and contours the plant of the foot section and the upper part of the foot section, configured to restrict the movement of subject plantar flexion, namely eversion/inversion movements, wherein the first zone (namely, foot section of high compression) and the second zone of high compression (namely, leg section of high compression) are bound by a vertical band, preferably with moderate compression, (band 1, FIGS. 1 and 3), wherein such vertical band accompanies laterally the peroneal alignment path of the subject ending in the fixation band, wherein the remaining zones are low compression zones, such that said low compression is lower compression than said high compression, such that said moderate compression is between said low and high compression.

The sock of the present disclosure has an heterogenous compression, this heterogeneous compression prevents ankle injury without affecting the normal movement of the lower limb, these different compression zones also avoid the formation/evolution of edema after injury. Surprisingly, the sock of the present disclosure could be use in sports, namely soccer without affecting the player performance. The sock of the present disclosure also improves blood circulation.

In an embodiment for better results, the compression between the leg to the foot section is heterogeneous.

In an embodiment for better results, the mean compression since the foot to the leg section is decreasing between sections [foot (more compression)/leg (less compression)] and it is heterogeneous within each section.

In an embodiment for better results, the sock of the present disclosure the reaming zones are low compression zone.

In an embodiment for better results, other sock of the present disclosure the zones identified by the letters A, B and C (zone A, Zone B and Zone C—FIG. 9) present a decreasing mean pressure from distal to proximal. In each zone, the regions with bands 1, 2a, 2b, 2c and 3 present greater compression compared to the remaining surfaces of the zone in which they are inserted.

In an embodiment for better results, the compression since the leg to the foot section is heterogeneous, i.e the pressure between the malleoli and the Achilles tendon is different, in different location allowing an heterogeneous pressure drop in the lower limb preventing sprain and/or the extent of damage after the schemia or ankle sprain.

In an embodiment for better results, the zone of high compression comprises at least a compression of 30 mmHg, preferably at least 40 mmHg (FIG. 9).

In an embodiment for better results, in the zone of high compression the compression (Zone A) may vary between 22 to 30 mmHg (FIG. 9).

The compression of the sock may be measure for different methodologies/devices, in the present disclosure it was use the pressure measuring device—MST MK V, from SwissLastic, Switzerland.

In an embodiment for better results, the compressing of the moderate compression zone (Zone B) may vary between 18 to 22 mmHg (FIG. 9).

In an embodiment for better results, the compressing of the zone of low compression (Zone A) may vary between 14 to 18 mmHg (FIG. 9).

In an embodiment for better results, the sock of the present disclosure may comprise two parallel vertical band (Band 1, FIGS. 1 and 3).

In an embodiment for better results, the vertical band of the leg elongates until the plant of the foot.

In an embodiment for better results, the sock of the present disclosure wherein the vertical band connects until the band 2b and 2c, near the plantar surface (FIGS. 1, 3 and 5).

In an embodiment for better results, the sock of the present disclosure may comprise a non-slipping area in the plant of the foot section (FIG. 5).

In an embodiment for better results, the sock of the present disclosure may comprise a resilient elastic material and a natural or synthetic fibre.

In an embodiment for better results, the sock of the present disclosure wherein the natural or synthetic fibre may be selected from cotton, wool, silk, microfiber, polyamide, or combinations thereof.

In an embodiment for better results, the resilient elastic material is selected from latex, a polyurethane-polyurea copolymer, spandex, elastane, nylon, neoprene, lycra, polyester, or combinations thereof.

In an embodiment for better results, the sock of the present disclosure may comprise a mixture of 4-7% (w/w) of elastane and 93-96% of polyamide fibres.

In an embodiment for better results, the sock of the present disclosure may comprise a section for the fingers.

In an embodiment for better results, the sock of the present disclosure the leg section may extend until the knee.

In an embodiment for better results, the sock of the present disclosure may comprise at least 3 levels of compression:

Level I=low→4 14 to 18 mmHg;
Level II=moderate→4 18 to 22 mmHg;
Level III=high→4 22 to 30 mmHg.

In an embodiment for better results, the sock of the present disclosure can achieve several levels of prevention:

Primary prevention—the sock of the present disclosure may prevent/remove an individual's exposure to a risk factor before he or she experiences their first ankle sprain. On the other hand, bandages and supports, due to their discomfort and associated costs, are not usually seen as primary prevention measures.

Secondary prevention—the sock of the present disclosure will allow the clinical evolution of individuals who have suffered an ankle sprain, with the advantage of favouring an active joint control by the neuromuscular apparatus of the individual, which contrasts with the predominantly passive stabilization of the rigid ankle supports.

Tertiary prevention—the sock of the present disclosure may reduce the social and economic costs of disease states in the population through early rehabilitation/reintegration and the enhancement of the remaining functional capacity of individuals. Because it is a stabilizing method with heterogeneous compressive characteristics, with peri malleolar compression contours, the oedema will be reduced in the regions of ligament injury. The existing methods do not show a marked selectivity in the regions where they promote tissue compression, so these new socks also stand out in this field.

The sock of the present disclosure can further present several advantages related to sports performance:

Velocity—These socks will allow an improvement in the speed of start, braking and changes of direction, since they have in the outer plantar face, areas of adhesion to the sports footwear decreasing the slip of the foot in the footwear. The fact of having these areas of adhesion only on the outside of the stocking, guarantees the comfort of the individual. On the other hand, ankle bandages and ankle support aim only at a protective goal, failing to meet the needs of the athlete regarding sports performance.

Fatigue resistance/endurance—The fact that all the sock is designed with compressive characteristics up to the knee region (in its longest version) favours venous return, assisting the muscular pump of the sural triceps, and thus reducing the fatigue associated with the accumulation of metabolites due to exercise. On the other hand, ankle bandages and supports present a too selective compression for the ankle region, not promoting the venous return associated with the muscular pump of the sural triceps.

The sock of the present disclosure can further present several advantages related to comfort:

the sock of the present disclosure presents a superior comfort to the solutions in the market, since unlike the ankle bandages, they do not use adhesive material in contact with the skin, nor do they have rigid materials like some supports of the ankle. The fact of occupying only the space of a common sock within the footwear, fosters a greater comfort that contrasts with the one which is experienced when the other methods of containment (bandages and supports) are added to the common socks.

The sock of the present disclosure can further present several economic advantages:

Individual—the costs associated with acquiring these new socks will be lower than buying regular sports socks+ankle bandages or ankle support+compression shiners to improve venous return.

Sports/competitive—The acquisition of this new preventive method by clubs presents an advantage, as it will save the money spent on the acquisition of non-reusable material, like bandages. By encouraging a reduction in the number of injuries and their seriousness will reduce the cost with athletes out of competition, an impact of extreme importance mainly in professional clubs.

Health systems—These socks will be an important advance in effectively reducing the number of first sprains and recurrent sprains, as well as reducing the severity of those that cannot be avoided. Preventing the injury from occurring or decreasing its severity, we may be helping to avoid invasive surgical interventions (therapy used in 20% of the most serious cases)[10]. As a successful preventive method, it will reduce emergency care, as well as expensive and harmful diagnostic methods (x-rays and CT scans). Bandages and supports do not have such high popularity, and for that reason will not have such a significant impact on health systems.

The sock of the present disclosure can further present several advantages social advantages:

Due the socks are a piece of clothing usually used make them go unnoticed when used for clinical reasons in a non-sporting context, fostering the psychological well-being of the wearer. Contrary to what happens with ankle bandages or supports, which easily identify the individual as having functional limitation, socks do not impose this negative psychological connotation on the wearer, thus fostering social inclusion.

The sock of the present disclosure can further present several advantages ecological advantages:

the sock of the present disclosure is environmentally friendly solution as it is a reusable prevention method, avoiding glues. On the other hand, solutions such as functional bandages that do not allow their reuse and that use glues in their bands are completely disposable and non-transferable, which does not allow them to be a sustainable environmental solution.

BRIEF DESCRIPTION OF THE DRAWINGS

The following figures provide preferred embodiments for illustrating the disclosure and should not be seen as limiting the scope of invention.

FIG. 9: illustrates an embodiment of the pressure Zones with the different sizes of the architecture of the stabilizing bands of the present invention, wherein:

(1) represents U-shaped band that promotes supination/pronation control, (2a) represents a double U-shaped band that secures the band 1 and serves as anchorage for the bands 2b and 2c.

(2b+2c) X-shaped band that promotes eversion (2b)/inversion (2c) and plantar flexion (2a+2b+2c) control, (3) represents U-shaped band that promotes aduction/abduction control, (4) represents the zone of lower compression, (5) represents non-slipping area.

DETAILED DESCRIPTION

The present disclosure relates to a sock capable of providing additional protection for an ankle joint reducing the need for using an ankle guard/support.

This sock can be used for preventing and reducing the ankle sprain.

Compared to socks, the sock of the present disclosure has several advantages:

An advantage of the sock of the present disclosure is that it is reusable, do not lose their elastic and containment properties throughout the activity, do not require a qualified health professional for their application and can be used as many times as the user wishes, because they have finishes that give them comfort and durability during and between uses, thus avoiding zones of friction and aggression to the skin. On the other hand, adhesive functional bandages (existing solution) do not respond well to users' needs, since they are not reusable, they lose part of their stabilizing capacity during physical activity due to sweat, they need a health professional for their application and cannot be used very often due to the possibility of skin damage by the adhesive material.

Another advantage will be the high comfort of the sock of the present disclosure, which contrasts with the discomfort described by athletes when using ankle supports (associated with greater stabilization and rigidity of materials used in their manufacture).

Prevention—Through a double stabilization (passive and active). The passive stabilization will be obtained by the specific orientation of the fibres that compose them, contrary to the mechanism of injury (inversion and/or supination). On the other hand, the active muscular stabilization will be obtained by the different pressures and elasticities of material that will stimulate specific skin sensory receptors, thus increasing the afferent information to the central nervous system, facilitating the intrinsic muscular activation of the main evertors—muscles that actively control the injury mechanism;

Performance—Through traction/adhesion lines/zones on the plantar surface of the sock, fundamentally to improve the adhesion of the sock to the sports footwear, helping the starting, braking and changes of direction[11].

Figure 1:
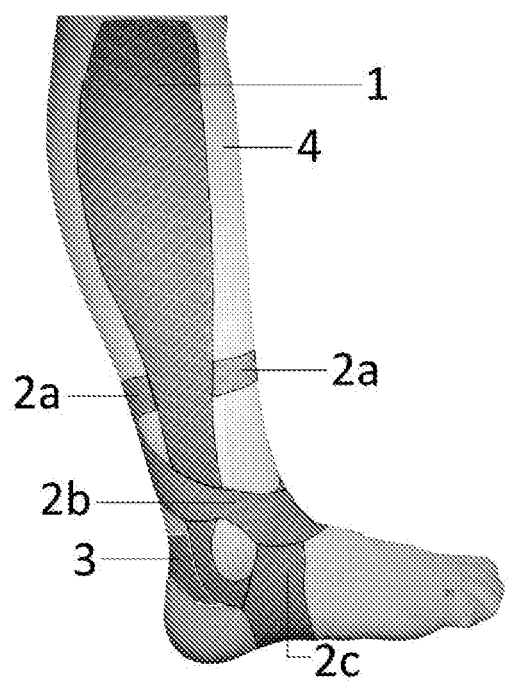
FIG. 1: illustrates a lateral view of the socks according to an embodiment of the present disclosure.

In an embodiment, FIG. 1 shows a lateral view of the socks of the present disclosure in the embodiment up to the knee, the socks have heterogenous compression. The zones of greater compression are identified with the numbers 1; 2a; 2b; 2c and 3. These are anatomic regions with important cutaneous and articular receptors, which benefit from extra compression. The band 1 (represents longitudinal U-shaped band), which accompanies laterally the peroneals muscle alignment, intends to create some resistance to pronosupination movements, so in its medial face the lever arm is smaller (50% of the total size of the band 1—external side), ending in a band of anchorage/fixation 2a. On the other hand, band 3 (represents transversal U-shaped band) is intended to minimize adduction/abduction movements, as is the case in functional bandages. In addition, the bands 2b and 2c (represents X-shaped band) together restrict the movement of plantar flexion as well as eversion/inversion, similar to the ankle supports, it's very important to note that the external width of the band 2c is thinner than band 2b in about 20% (FIGS. 1, 3 and 5), in order to create a greater resistance to the inversion movement. The regions with the number 4 are regions of lower compression compared to those described above.

Figure 2:
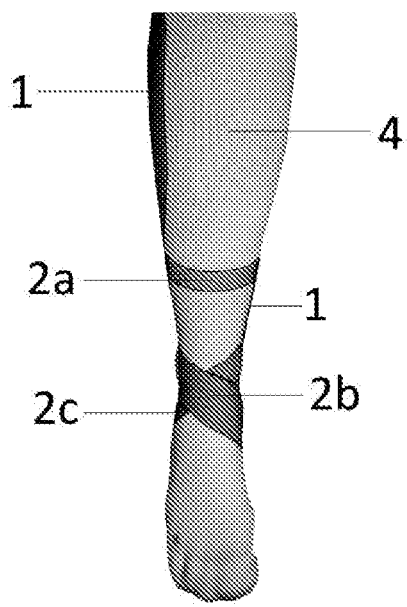
FIG. 2: illustrates an embodiment of an anterior view of the socks of the present disclosure.

In an embodiment, FIG. 2 shows an Anterior view of the socks of the most complete version (up to the knee), the socks will have heterogenous compression. The zones of greater compression are identified with the numbers 1; 2a; 2b; 2c and 3, and the 4 a zone of less compression. The band 1 (represents longitudinal U-shaped band), which accompanies laterally the path peroneals alignment, intends to create some resistance to pronosupination movements, so in its medial face the lever arm is smaller, (50% of the total size of the band 1—external side) ending in a band of anchorage/fixation 2a. In addition, the bands 2b and 2c (represents X-shaped band) together restrict the movement of plantar flexion as well as eversion/inversion, similar to the ankle supports, it's very important to note that the internal width of the band 2b is longer than its external component 2c in about 20%. The regions with the number 4 are regions of lower compression compared to those described above, avoiding too much compression on this region.

Figure 3:
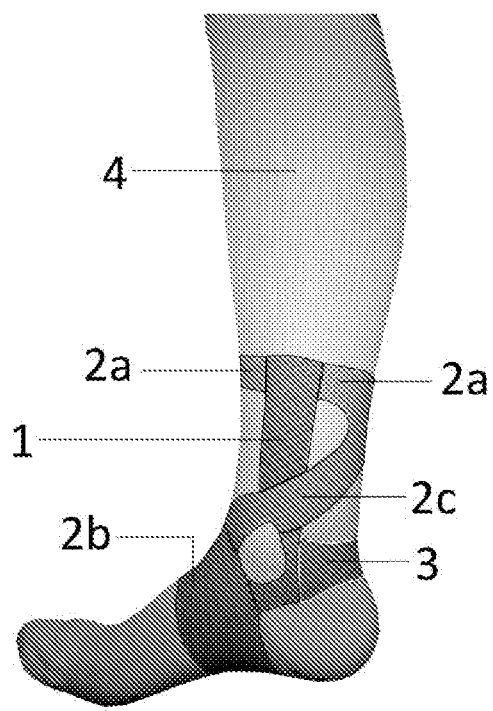
FIG. 3: illustrates an embodiment of a medial view of the socks of the present disclosure.

In an embodiment, FIG. 3 shows a Medial view of the socks of the most complete version (up to the knee), the socks will have heterogenous compression. The zones of greater compression are identified with the numbers 1; 2a; 2b; 2c and the 4 a zone of less compression. These are anatomic regions with important cutaneous and articular receptors, which benefit from extra compression. The band 1 (represents longitudinal U-shaped band), in its medial face the lever arm is smaller (50% of the total size of the band 1—external side), ending in a band of anchorage/fixation 2a and intends to create some resistance to pronosupination movements. On the other hand, band 3 (represents transversal U-shaped band) is intended to minimize adduction/abduction movements, as is the case in functional bandages. In addition, the bands 2b and 2c (represents X-shaped band) together restrict the movement of plantar flexion as well as eversion/inversion, similar to the ankle supports, it's very important to note that the internal width of the band 2b is longer than its external component 2c in about 20%, also has an advantage of protecting the internal plantar arch. The regions with the number 4 are regions of lower compression compared to those described above, avoiding too much compression on this region.

Figure 4:
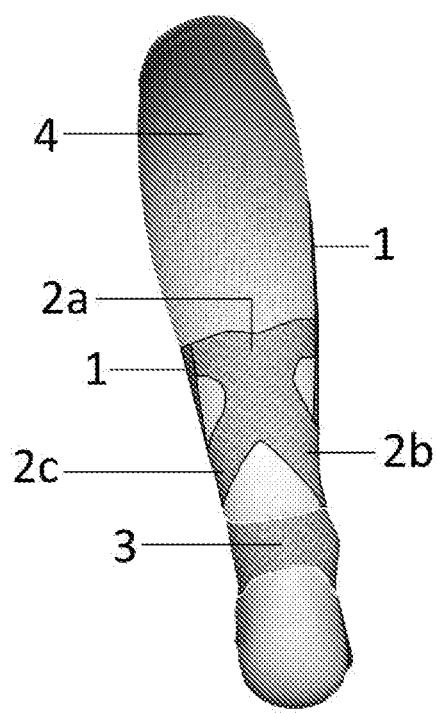
FIG. 4: illustrates an embodiment of a posterior view of the socks of the present disclosure.

In an embodiment, FIG. 4 shows a Posterior view of the socks of the most complete version (up to the knee), the socks will have heterogenous compression. The zones of greater compression are identified with the numbers 1; 2a; 2b; 2c and 3 and the 4 a zone of less compression. These are anatomic regions with important cutaneous and articular receptors, which benefit from extra compression. The band 1 (represents longitudinal U-shaped band), which accompanies laterally the path peroneals alignment, intends to create some resistance to pronosupination movements, so in its medial face the lever arm is smaller (50% of the total size of the band 1—external side), ending in a band of anchorage/fixation 2a, passing through the sole of the foot. On the other hand, band 3 (represents transversal U-shaped band) is intended to minimize adduction/abduction movements, as is the case in functional bandages. In addition, the bands 2b and 2c (represents X-shaped band) together restrict the movement of plantar flexion as well as eversion/inversion, similar to the ankle supports, it's very important to note that the internal width of the band 2b is longer than its external component in about 20%, also has an advantage of protecting the internal plantar arch. The regions with the number 4 are regions of lower compression compared to those described above, avoiding too much compression on this region.

Figure 5:
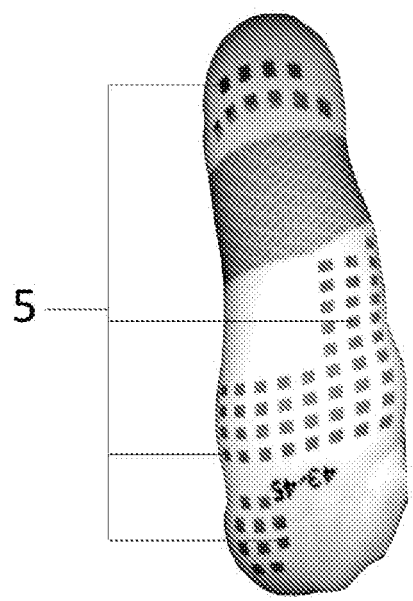
FIG. 5: illustrates an embodiment of plantar view of the socks of the present disclosure.

In an embodiment FIG. 5 shows a Plantar view of the socks. The number 5 represents the zones of greater adhesion of the plantar region to the footwear, key factor for optimization of the performance. However, they may be produced without this component.

Figure 6:
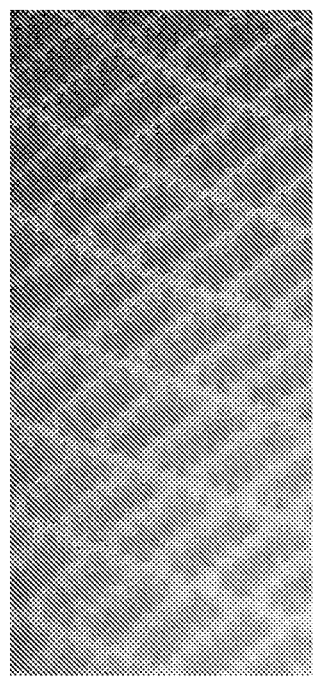
FIG. 6: illustrates an embodiment of an architecture of the stabilizing bands are rectangular shape of the present disclosure.
Figure 9:
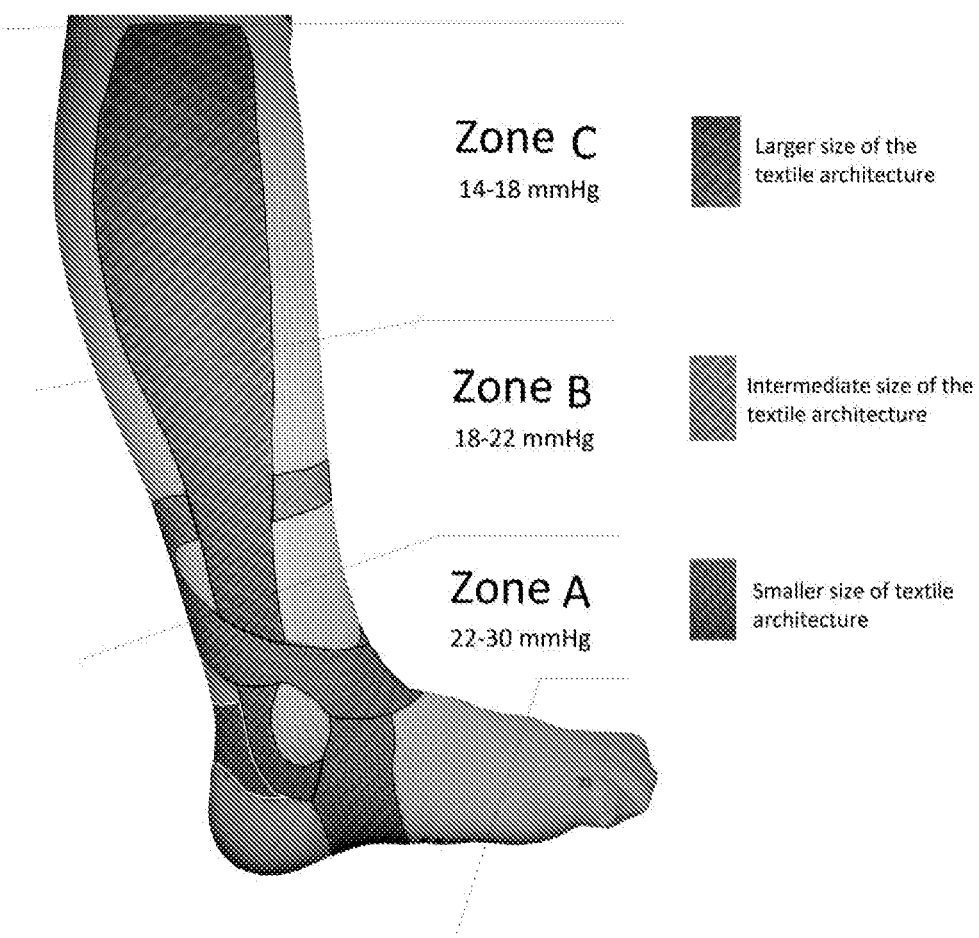

In an embodiment FIG. 6 shows an architecture of the stabilizing bands in a rectangular shape. To give the protective function was created a different textile architecture of rectangular shape, so as to be able to introduce the selective resistance intended, and at same time to give the fundamental flexibility for the movement of the foot. This architecture allows to induce different tensions in the bands according their dimensions and their functions, in certain specific places was decided to reduce the size and in others increase it (FIG. 9).

Figure 7:
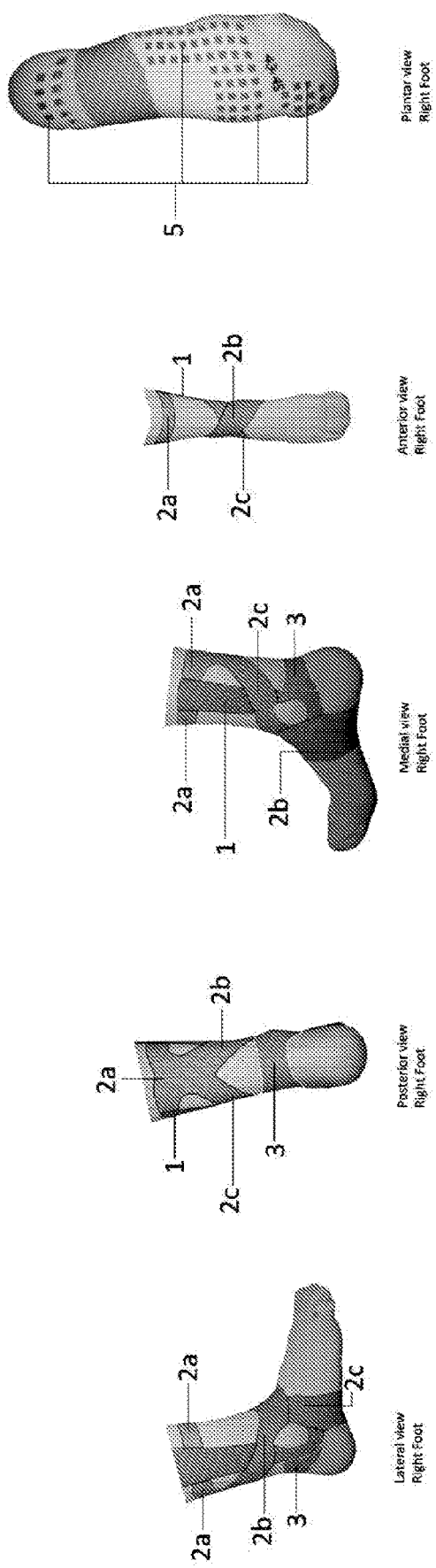
FIG. 7: illustrates an embodiment of a short socks of the present disclosure.

In an embodiment FIG. 7 shows a short socks version. The sock of the present disclosure can have a smaller version, structurally the only difference between the long socks and their shorter version is the length of the band 1 (lateral side) which will be reduced, thereby ending in the fixation band 2a.

Figure 8:
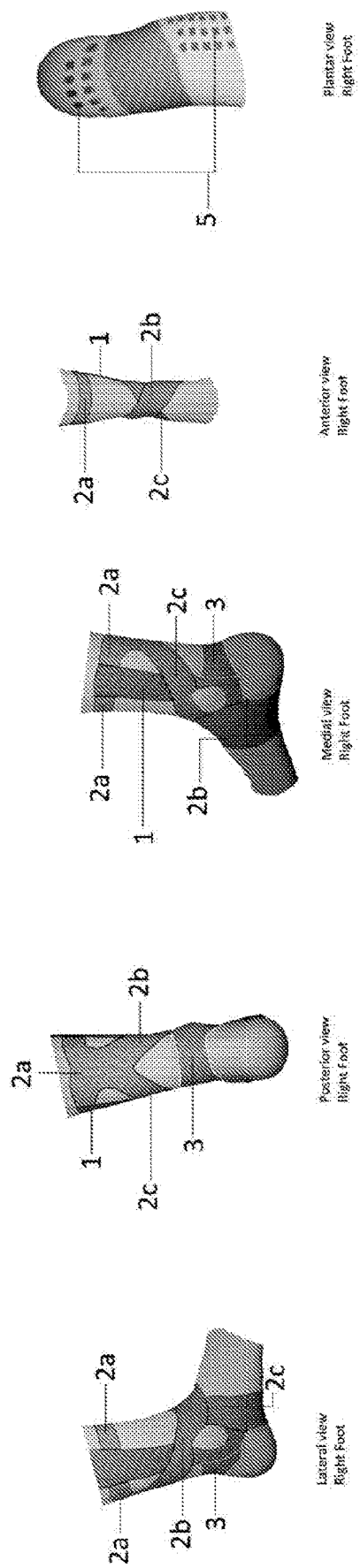
FIG. 8: illustrates an embodiment of short socks without fingers of the present invention.

In an embodiment FIG. 8 shows short socks without fingers view. The sock of the present disclosure can have a smaller version without fingers, structurally the two differences between the long socks and their shorter version is the length of the band 1 (lateral side) which will be reduced, thereby ending in the fixation band 2a and it is not closed on the toes. The option of being produced without the coating of fingers has the ultimate goal of responding to the needs and preferences of the user.

In an embodiment, the sock of the present disclosure has a decreasing compression (from distal to proximal) which will promote venous return, reducing fatigue, a predisposing factor for traumatic ligament injuries such as ankle sprain or muscle overload/overuse injuries.

In an embodiment, the sock of the present disclosure can have a smaller version (FIG. 7) and can be further produced with or without the finger coating (FIG. 8).

In an embodiment, structurally the only difference between the long socks and their shorter version is the length of the band 1 (lateral side) which will be reduced, thereby ending in the fixation band 2a. The option of being produced without the coating of fingers has the ultimate goal of responding to the needs and preferences of the user.

In an embodiment, the sock of the present disclosure may have an heterogenous compression in the different Zones (A, B, C FIG. 9) where the greater compression is identified with the numbers 1; 2a; 2b; 2c and 3. These are anatomic regions with important cutaneous and articular receptors, which benefit from extra compression:

The band 1, which accompanies laterally of the path peroneal alignment, it is able to create resistance to prono-supination movements, so in its medial face the lever arm is smaller (50% of the total size of the band 1—external side) an increase of the size of the textile architecture, ending in a band of anchorage/fixation 2a. This fixation band 2a may be incorporated in double U-shaped. The band 3 is configured to minimize adduction/abduction movements, as is the case in functional bandages (FIG. 4).

In addition, the bands 2a and 2c together restrict the movement of plantar flexion as well as eversion/inversion, similar to the ankle supports (FIGS. 2 and 4).

The regions with the number 4 are regions of lower compression compared to those described above, avoiding too much compression on this region. Finally, number 5 represents the zones of greater adhesion of the plantar region to the footwear, key factor for optimization of the performance.

In an embodiment, in the version of the sock "up to the knee", the sock will have heterogenous compression. The zones of greater compression are identified with the numbers 1; 2a; 2b; 2c and 3. These are anatomic regions with important cutaneous and articular receptors, which benefit from extra compression. The band 1, which accompanies laterally the path peroneals alignment, intends to create some resistance to pronosupination movements, so in its medial face the lever arm is smaller, ending in a band of anchorage/fixation 2a. On the other hand, band 3 is intended to minimize adduction/abduction movements, as is the case in functional bandages (FIG. 4). In addition, the bands 2a and 2c together restrict the movement of plantar flexion as well as eversion/inversion, similar to the ankle supports (FIG. 4). The regions with the number 4 are regions of lower compression compared to those described above, being important for example to maintain a correct blood flow to the Achilles tendon, avoiding too much compression on this region. Finally, number 5 represents the zones of greater adhesion of the plantar region to the footwear, key factor for optimization of the performance.

In an embodiment for better results, the sock of the present disclosure has a decreasing compression (from distal to proximal) which will promote venous return, reducing fatigue, a predisposing factor for traumatic ligament injuries such as ankle sprain or muscle overload/overuse injuries.

In an embodiment, the sock of the present disclosure can have a smaller version (FIG. 7) and can be further produced with or without the finger coating (FIG. 8).

In an embodiment, structurally the only difference between the long socks and their shorter version is the length of the band 1 (lateral side) which will be reduced, thereby ending in the fixation band 2a. The option of being produced without the coating of fingers has the ultimate goal of responding to the needs and preferences of the user.

In an embodiment, the sock of the present disclosure may comprise areas of external plantar adhesion. However, they may be produced without this component.

In an embodiment, spending on the risk of injury or personal preference, these the sock of the present disclosure may comprise 3 compression zones: low, moderate or high (14-18 mmHg, 18-22 mmHg, 22-30 mmHg, respectively) (FIG. 9).

The term "comprising" whenever used in this document is intended to indicate the presence of stated features, integers, steps, components, but not to preclude the presence or addition of one or more other features, integers, steps, components or groups thereof.

The disclosure should not be seen in any way restricted to the embodiments described and a person with ordinary skill in the art will foresee many possibilities to modifications thereof. The above described embodiments are combinable. The following claims further set out particular embodiments of the disclosure.

REFERENCES

1—Yeung M S, Chan K M, So MPhil C H, Yuan W Y. An epidemiological survey on ankle sprain. *British Journal of Sports Medicine* 1994; 28(2):112-6.

2—Fong D T, Hong Y, Chan L K, Yung P S, Chan K M. A systematic review on ankle injury and ankle sprain in sports. *Sports Medicine* 2007; 37(1):73-94.

3—Kemler E, Krist M R, G I van de Port I, Hoes A W, de Wit G A, Backx F J G. Economic Evaluation of a Soft Ankle Brace Compared to Tape in Acute Lateral Ankle Ligamentous Sprains. *Clinical Research on Foot & Ankle* 2016; 04(04).

4—Pourkazemi F, Hiller C E, Raymond J, Nightingale E J, Refshauge K M. Predictors of chronic ankle instability after an index lateral ankle sprain: a systematic review. *J Sci Med Sport* 2014; 17(6):568-73.

5—Doherty C, Delahunt E, Caulfield B, Hertel J, Ryan J, Bleakley C. The incidence and prevalence of ankle sprain injury: a systematic review and meta-analysis of prospective epidemiological studies. *Sports Med* 2014; 44(1): 123-40.

6—Boer A S D, Schepers T, Panneman M, J M, Beeck E F V, Lieshout E M V. Health care consumption and costs due to foot and ankle injuries in the Netherlands, 1986-2010. *BMC Musculoskeletal Disorders* 2014; 15(128):1-10.

7—Karlsson J, Verhagen E, Beynnon B D, Amendola A. Preventing ankle injuries. In: Engebretsen L, editor. Handbook of sports Medicine and Science, Sports Injury Prevention. Oxford: Blackwell Publishing; 2009. p. 30-48.

8—Dizon J M, Reyes J J B. A systematic review on the effectiveness of external ankle supports in the prevention of inversion ankle sprains among elite and recreational players. *Journal of Science and Medicine in Sport* 2010; 13:309-17.

9—Evans U, Clough A. Prevention of ankle sprain: A systematic review. *International Musculoskeletal Medicine* 2013; 34(4):146-58.

10—Baumhauer J F, O'Brien T. Surgical Considerations in the Treatment of Ankle Instability. *Journal of Athletic Training* 2002; 37(4):458-62.

11—Silva D C F, Santos R, Vilas-Boas J P, Macedo R, Montes A, Sousa A S P. Influence of cleats-surface interaction on the performance and risk of injury in soccer: a systematic review. *Applied Bionics and Biomechanics In press.*

The invention claimed is:

1. A sock for preventing ankle injury of a subject, comprising:
   a sock body which includes a leg section and a foot section,
   a first fixation band positioned in the leg section and oriented in a transverse direction perpendicular to a longitudinal orientation of the leg applying a first zone of high compression configured to contour the leg, a fixation band having a single or double U-shape,
   a second band positioned at the foot section applying a second zone of high compression positioned to match a back of the ankle of the subject and configured to minimize adduction/abduction movements of the subject;
   a third band positioned at a third zone of high compression joining the subject leg section and foot section, the third band having two parts coupled in an X-shape with one end at the fixation band and contouring the plant of the foot section and the upper part of the foot section, the third zone of high compression being configured to restrict the movement of plantar flexion of the subject,
   a fourth vertical band coupling the first and second bands in a region of moderate compression, the fourth band laterally adjacent to a peroneal alignment path of the subject ending at the fixation band,
   wherein remaining zones are low compression zones such that said low compression is lower compression than said high compression and such that said moderate compression is between said low and high compression;
   wherein the compression between the leg section and the foot section is heterogeneous;
   wherein the compression in the leg section is less than the compression in the foot section.

2. The sock according to claim 1, wherein a magnitude of compression of the zone of high compression is at least 30 mmHg.

3. The sock according to claim 1, wherein a magnitude of compression of the zone of high compression varies between 22 to 30 mmHg.

4. The sock according to claim 1, wherein a magnitude of compression of the moderate compression varies between 18 to 22 mmHg.

5. The sock according to claim 1, wherein a magnitude of compression of the low compression varies between 14 to 18 mmHg.

6. The sock according to claim 1, further comprising a non-slipping area in a plant of the foot section.

7. The sock according to claim 1, wherein the sock comprises a resilient elastic material and a natural or synthetic fibre.

8. The sock according to claim 7, wherein the natural or synthetic fibre is selected from the group consisting of: cotton, wool. silk, microfiber. polyamide, and combinations thereof.

9. The sock according to claim 7, wherein the resilient elastic material is selected from the group consisting of: natural latex. a polyurethane-polyurea copolymer. spandex, elastane, nylon, neoprene, lycra, polyester, and combinations thereof.

10. The sock according to claim 7, wherein the sock is composed of a mixture of 4-7% (w/w) of elastane and 93-96% of polyamide fibres.

11. The sock according to claim 1, further comprising a section for toes.

12. The sock according to claim 1, wherein the leg section extends until a knee of the subject.

* * * * *